United States Patent
Yuan

(10) Patent No.: US 10,507,188 B2
(45) Date of Patent: Dec. 17, 2019

(54) PARTICLES CONTAINING AN OPIOID RECEPTOR ANTAGONIST AND METHODS OF USE

(71) Applicant: UNIVERSITY OF CHICAGO, Chicago, IL (US)

(72) Inventor: Chun-Su Yuan, Chicago, IL (US)

(73) Assignee: The University of Chicago, Chicago, IL (US)

( * ) Notice: Subject to any disclaimer, the term of this patent is extended or adjusted under 35 U.S.C. 154(b) by 115 days.

(21) Appl. No.: 15/835,181

(22) Filed: Dec. 7, 2017

(65) Prior Publication Data

US 2018/0098947 A1    Apr. 12, 2018

Related U.S. Application Data

(63) Continuation of application No. 13/001,146, filed as application No. PCT/US2009/047372 on Jun. 15, 2009, now abandoned.

(60) Provisional application No. 61/077,242, filed on Jul. 1, 2008.

(51) Int. Cl.
- *A61K 31/485* (2006.01)
- *A61K 9/51* (2006.01)
- *A61K 31/00* (2006.01)

(52) U.S. Cl.
CPC ............ *A61K 31/00* (2013.01); *A61K 9/5138* (2013.01); *A61K 9/5161* (2013.01); *A61K 31/485* (2013.01)

(58) Field of Classification Search
CPC .................................................. A61K 31/485
See application file for complete search history.

(56) References Cited

U.S. PATENT DOCUMENTS

| | | | |
|---|---|---|---|
| 3,723,440 A * | 3/1973 | Freter .................. | A61K 31/395 546/97 |
| 5,723,269 A | 3/1998 | Akagi et al. | |
| 5,981,474 A | 11/1999 | Manning et al. | |
| 6,274,591 B1 | 8/2001 | Foss et al. | |
| 6,419,959 B1 | 7/2002 | Walter et al. | |
| 6,608,075 B2 * | 8/2003 | Foss ..................... | A61K 31/485 514/282 |
| 7,572,463 B2 | 8/2009 | Bartholomaeus et al. | |
| 2002/0032166 A1 | 3/2002 | Shefter et al. | |
| 2003/0229111 A1 | 12/2003 | Oshlack et al. | |
| 2004/0167147 A1 | 8/2004 | Foss et al. | |
| 2004/0247683 A1 | 12/2004 | Popescu et al. | |
| 2004/0266806 A1 | 12/2004 | Sanghvi et al. | |
| 2005/0004155 A1 | 1/2005 | Boyd et al. | |
| 2008/0075771 A1 | 3/2008 | Vaughn et al. | |

FOREIGN PATENT DOCUMENTS

| | | |
|---|---|---|
| EP | 0860166 | 8/1998 |
| WO | WO 2001/085257 | 11/2001 |
| WO | WO 2004/091665 | 10/2004 |
| WO | WO 2007/053698 | 5/2007 |

OTHER PUBLICATIONS

Chang, RK, et al. "Polymethacrylates." Handbook of Pharmaceutical Excipients (2009) 525-533.*
Janes, Kevin A., et al. "Chitosan nanoparticles as delivery systems for doxorubicin." Journal of controlled Release 73.2-3 (2001): 255-267.*
Ko, J. A., et al. "Preparation and characterization of chitosan microparticles intended for controlled drug delivery." International journal of pharmaceutics 249.1-2 (2002): 165-174.*
Yuan, Chun-Su, et al. "Effects of enteric-coated methylnaltrexone in preventing opioid-induced delay in oral-cecal transit time." Clinical Pharmacology & Therapeutics 67.4 (2000): 398-404.*
"Alvimopan, ADL Aug. 2698, ADL 82698, Entrareg, LY 246736," *Drugs R D*, 7(4):245-253, (2006).
"The United States Pharmacopeia: The National Formulary," *Rockville: United States Pharmacopeial Convention, Inc.* pp. 1793-1799, 1995.
Anal et al., "Ionotropic cross-linked chitosan microspheres for controlled release of ampicillin," *International Journal of Pharmaceutics*, 312:166-173, (2006).
Beck et al., "Nanoparticle-coated microparticles: preparation and characterization," *J Microencapsulation*, 21:499-512, 2004.
Calvo et al., "Novel hydrophilic chitosan-polyethylene oxide nanoparticles as protein carriers," *J Appl Pol Sci.*, 63:125-132, 1997.
Falk et al., "Controlled release of ionic compounds from poly (l-lactide) microspheres produced by precipitation with a compressed antisolvent," *Journal of Controlled Release*, 4491):77-85, 1997.
Fernandez-Urrusuno et al., "Enhancement of nasal absorption of insulin using chitosan nanoparticles," *Pharm Res.*, 16:1576-1581, 1999.
Gan et al., "Modulation of surface charge, particle size and morphological properties of chitosan—TPP nanoparticles intended for gene delivery," *Colloids and Surfaces B: Biointerfaces*, 44:65-73, (2005).
Janes et al., Chitosan nanoparticles as delivery systems for doxorubicin, *Journal of Controlled Release*, 73:255-267, (2001).
Nobs et al., "Surface modification of poly(lactic acid) nanoparticles by covalent attachment of thiol groups by means of three methods," *International Journal of Pharmaceutics*, 250:327-337, 2003.
Osinski et al., "Determination of methylnaltrexone in clinical samples by solid-phase extraction and high-performance liquid chromatography for a pharmacokinetics study," *J. Chromatogr. B*, 780:251-259, 2002.

(Continued)

*Primary Examiner* — Bethany P Barham
*Assistant Examiner* — Peter Anthopolos
(74) *Attorney, Agent, or Firm* — Norton Rose Fulbright US LLP

(57) ABSTRACT

Particles comprising an opioid receptor antagonist as well as methods of their use and methods of their preparation are provided herein. Such particles may be used for treating and preventing opioid-induced side effects in patients, and may be provided to chronic opioid users as well.

9 Claims, 1 Drawing Sheet

(56) References Cited

OTHER PUBLICATIONS

Reichle and Conzen, "Methylnaltrexone—a new peripheral μ-receptor antagonist for the prevention and treatment of opioid-induced extra cerebral side effects," *Current Opinion in Investigational Drugs*, 9(1): 11 pages, 2008.

Sarmento et al., "Oral bioavailability of insulin contained in polysaccharide nanoparticles," *Biomacromolecules*, 8:3054-3060, 2007.

Sinha et al., "Chitosan microspheres as a potential carrier for drugs," *International Journal of Pharmaceutics*, 274:1-33, (2004).

Summons to Attend Oral Proceedings for EP 09774028.6, dated Feb. 24, 2016.

Supplementary European Search Report issued in European application No. EP 09 77 4028, dated Jul. 21, 2011.

Wikipedia contributors, "Chitosan," *Wikipedia, The Free Encyclopedia*, http://en.wikipedia.org/w/index.php?title=Chitosan&oldid=434999103 (accessed Jun. 23, 2011).

Yuan et al., "Effects of enteric-coated methylnaltrexone in preventing opioid-induced delay in oral-cecal transit time," *Clin Pharmacol. Ther.*, 67:398-404, 2000.

Yuan et al., "Methylnaltrexone, a novel peripheral opioid receptor antagonist for the treatment of opioid side effects," *Expert Opin. Investig. Drugs*, 15(5): 541-552, (2006).

Yuan et al., "The safety and efficacy of oral methylnaltrexone in preventing morphine-induced delay in oral-cecal transit time," *Clin Pharmacol Ther*, 61:467-475, 1997.

* cited by examiner

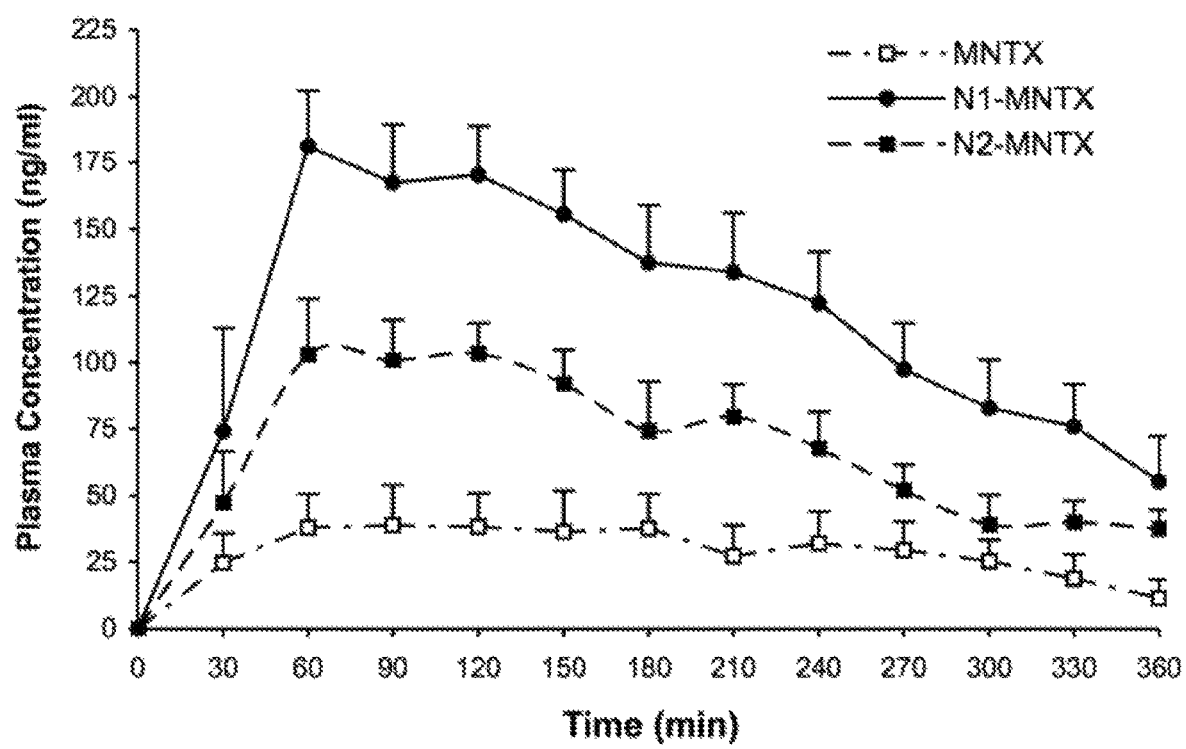

PARTICLES CONTAINING AN OPIOID RECEPTOR ANTAGONIST AND METHODS OF USE

CONTINUING DATA

The present application is a continuation from U.S. application Ser. No. 13/001,146 filed May 18, 2011, which is a 371 national stage entry of PCT/US09/47372 filed Jun. 15, 2009, which claims the benefit of priority to U.S. Application No. 61/077,242, filed Jul. 1, 2008; the entire contents of each application being incorporated by reference.

BACKGROUND OF THE INVENTION

1. Field of the Invention

The present invention relates to the fields of opioid receptor antagonists and drug delivery. In general, particles comprising an opioid receptor antagonist are described along with methods of their use.

2. Description of Related Art

Opioids are effective analgesics. However, their use is associated with a number of undesirable side effects. One such effect is constipation. Opioid-induced changes in gastrointestinal motility are almost universal when these drugs are used to treat pain, and at times may limit their use, leaving the patient in pain. Common treatments of bulking agents and laxatives have limited efficacy and may be associated with side effects such as electrolyte imbalances.

One treatment for opioid side effects is the use of opioid receptor antagonists which cross the blood-brain-barrier, or which are administered directly into the central nervous system. Opioid receptor antagonists such as naltrexone and naloxone have been administered intramuscularly or orally to treat opioid induced side effects. Naltrexone and naloxone are highly lipid soluble and rapidly diffuse across biological membranes, including the blood-brain barrier. However, naltrexone, naloxone, nalmefene, and other opioid receptor antagonists which may reverse many opioid side effects have a narrow therapeutic window before they are observed to reverse the desired analgesic effect of the opioid being used.

Many quaternary amine opioid receptor antagonist derivatives, such as methylnaltrexone (MNTX), do not reduce the analgesic effect of opioids when administered peripheral to the central nervous system. These quaternary amine opioid receptor antagonist derivatives, which have a relatively higher polarity and reduced lipid solubility when compared to the tertiary forms of the drugs, were specifically developed to not traverse the blood-brain barrier or to traverse it at a greatly reduced rate. However, high levels of MNTX in the plasma can lead to undesirable side effects such as orthostatic hypotension.

In April 2008, the United States FDA approved the use of methylnaltrexone bromide (Relistor™) as a subcutaneous injection to help restore bowel function in patients with late-stage, advanced illness who are receiving opioids on a continuous basis to help alleviate their pain. In particular, the drug is designed to alleviate constipation in patients who have not successfully responded to laxative therapy.

Alternative methods of providing methylnaltrexone and other opioid receptor antagonists to patients are desirable, such as methods that allow lower doses of the antagonist to be delivered but with comparable efficacy, and methods less intrusive than subcutaneous injection.

SUMMARY OF THE INVENTION

The present invention provides methods and compositions involving particles comprising an opioid receptor antagonist. In some embodiments, these particles allow for enhanced effects on opioid-induced bowel dysfunction and other indications. For example, particles of the present invention may result in improved absorption of the opioid receptor antagonist into the circulatory system compared to traditional formulations, thus resulting in a decrease in the dose required to reach therapeutic plasma levels. The particles may also be employed in preventative methods as well, such as to prevent opioid-induced side effects. Moreover, the opioid responsible for the opioid-induced effects may be an exogenously administered opioid, or an endogenous opioid that is produced by a patient in response to, for example, abdominal surgery. Chronic opioid users may also benefit from receiving particles of the present invention. Particles may comprise enteric coatings and/or time-release agents to assist in targeted or controlled absorption of the opioid receptor antagonist.

As explained in further detail below, a particle may comprise only one type of particle ("homoparticulate"), or a particle may comprise two or more types of particles ("heteroparticulate"). Accordingly, the term "particle" encompasses both homo- and heteroparticulate particles. A "type" of particle refers to a particle comprising a particular set of ingredients. Thus, two different types of particles will have two different sets of ingredients (e.g., one particle comprises an opioid receptor antagonist and one particle does not). If two particles contain the same ingredients but the ratio of ingredients differs, the two particles are still considered to be of the same "type."

As will be explained, it is to be understood that a particle of the present invention comprising an opioid receptor antagonist may include, but is not limited to, a homoparticulate particle, a heteroparticulate particle, a particle that comprises a single particle, a particle that comprises two or more particles, an enterically coated particle, a particle comprising a time-release agent, or a particle comprising any other property or ingredient described herein or any combination of these properties or ingredients, except for combinations of particles whose definitions (provided below) are mutually exclusive (e.g., a particle cannot simultaneously be a homoparticulate particle and a heteroparticulate particle). Any of these particles may be comprised in a pharmaceutical composition, as described herein, and/or may be employed in any methods of making, administration, and/or use as described herein.

Accordingly, one general aspect of the present invention contemplates a particle comprising an opioid receptor antagonist. Opioid receptor antagonists are described herein. Another general aspect of the present invention contemplates a particle comprising an opioid receptor antagonist and chitosan. Yet another general aspect of the present invention contemplates an enterically coated particle that comprises at least one opioid receptor antagonist. Any particle discussed herein may further comprise at least one additive. Such additives are described herein. The diameter of any particle described herein may be between about 30-1000 nm or higher, as that range is described herein. In certain embodiments, a homoparticulate particle is contemplated. In certain embodiments, a heteroparticulate particle is contemplated.

An opioid receptor antagonist that is comprised in any particle of the present invention may be, for example, a peripheral opioid antagonist. In certain embodiments, the opioid receptor antagonist may be a quaternary or tertiary morphinan derivative, a piperidine-N-alkylcarboxylate, a carboxy-normorphinan derivative, or a quaternary benzomorphan. The quaternary morphinan may be, for example, a quaternary salt of N-methylnaltrexone, N-methylnaloxone, N-methylnalorphine, N-diallylnormorphine, N-allyllevellorphan, or N-methylnalmefene. In particular embodiments, the peripheral opioid receptor antagonist is methylnaltrexone. In certain embodiments, a particle comprises two or more opioid receptor antagonists. In certain embodiments, the weight percentage of total opioid receptor antagonist in the particle ranges from about, at most about, or at least about 0.1-30%. In certain embodiments, the weight percentage of total opioid receptor antagonist is about 0.1%, 0.25%, 0.5%, 0.75%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any range derivable therein. The weight percentage of total opioid receptor antagonist in the particle may range higher than 30%, in certain embodiments. In certain embodiments, the weight percentage may be about, at least about, or at most about 35%, 40%, 45%, 50%, 55%, 60%, 65%, 70%, 75%, 80%, 85%, 90%, 95%, or 99%, or any range derivable therein.

As noted above, a particle of the present invention may comprise an additive. Additives that may be employed are described herein. An additive may comprise a polymer. An additive may comprise, for example, a polysaccharide. An additive may comprise, for example, a polyphosphate. In certain embodiments, at least one additive is a hydrophobic additive. Hydrophobic additives are defined herein. In certain embodiments, at least one additive is a hydrophilic additive. Hydrophilic additives are defined herein. More than one additive may be employed, as described herein. For example, a particle may comprise at least two hydrophilic additives. A hydrophilic additive may, for example, be positively charged at acidic and neutral pH. Acidic pH refers to a pH of less than 7.0. In certain embodiments, "acidic pH" refers to about or at most about 6.5, 6.0, 5.5, 5.0, 4.5, 4.0, 3.5, 3.0, 2.5, 2.0, 1.5, 1.0, 0.5 or lower, or any range derivable therein. A hydrophilic additive that is positively charged at acidic and neutral pH may be, for example, chitosan. Neutral pH refers to a pH of about 7.0. In certain embodiments, a hydrophilic additive may be negatively charged at basic and neutral pH. As used herein, a basic pH refers to a pH of greater than 7.0. In certain embodiments, "basic pH" refers to about or at least about 7.5, 8, 8.5, 9, 9.5, 10, 10.5, 11, 11.5, 12, 12.5, 13, 13.5, 14, or higher, or any range derivable therein. A hydrophilic additive may be negatively charged at acidic and neutral pH, in certain embodiments. Such an additive may be, for example, a polyphosphate, such as pentasodium tripolyphosphate (TPP). In certain embodiments, at least one hydrophilic additive is a hydrophilic additive that is positively charged at acidic and neutral pH, and at least one second hydrophilic additive is further defined as a hydrophilic additive that is negatively charged at acidic and neutral pH. In certain embodiments, two hydrophilic additives employed in a particle of the present invention are chitosan and TPP.

Ratios of additives that may be used in particles of the present invention are described herein. For example, the ratio of chitosan:TPP may range between about 5:9 to about 50:9 (w/w). In certain embodiments, the ratio of chitosan:TPP:opioid receptor antagonist is between about 5:9:4 to 50:9:32 (w/w/w). In certain embodiments, the ratio of chitosan:TPP:opioid receptor antagonist is between about 5:9:4 to 50:9:32 (w/w/w). In certain embodiments, the ratio of chitosan:TPP:opioid receptor antagonist is between about 25:9:4 and 25:9:32 (w/w/w). In certain embodiments, the ratio of chitosan:TPP:opioid receptor antagonist is about 5:1.8:3.2 (w/w/w).

Any particle of the present invention may comprise an enteric agent, as described herein. Accordingly, any particle of the present invention may be comprised in an enteric coating to form an enterically coated particle. As noted above, an enterically coated particle may have a diameter of about 30-1000 nm, as that range is described herein. In certain embodiments an enterically coated particle has a diameter of about 200-500 nm, as that range is described herein. An enterically coated particle may comprise any polymer described herein, such as a Eudragit® polymer (e.g., Eudragit® L100 or Eudragit® S100). An enteric coating may comprise, e.g., an acetylated monoglyceride, such as a Myvacet™ distilled acetylated monoglyceride. Such acetylated monoglycerides are known in the art, and include, e.g., Myvacet™ 9-45. Combinations of agents may be comprised within an enteric coating of the present invention. For example, a Eudragit® polymer and a Myvacet™ distilled acetylated monoglyceride may be comprised in an enteric coating of an enterically coated particle of the present invention. The mesh fraction of the enterically coated particle may, in certain embodiments, range from about +40 to +90 mesh fraction (e.g., +40, +50, +60, +70, +80, +90, or any range derivable therein).

Pharmaceutical compositions that comprise a particle of the present invention are also described herein. Such pharmaceutical compositions typically comprise at least one pharmaceutically acceptable carrier. Particles of the present invention may be comprised in a suspension and as such, the present invention contemplates pharmaceutical compositions comprising a particle of the present invention, wherein the particle is comprised in a suspension. Any pharmaceutical composition that comprises a particle may be further defined as an orally administerable pharmaceutical composition. The orally administerable pharmaceutical composition may, in certain embodiments, be comprised in a suspension or capsule. The orally administerable pharmaceutical composition may further comprise a flavoring agent. A pharmaceutical composition that comprises a particle of the present invention may be further defined as a time release pharmaceutical composition, wherein the time release pharmaceutical composition is formulated to release the opioid receptor antagonist over time. Particles comprised in a pharmaceutical composition may comprise any additive described herein, such as a polyanionic additive (e.g., pentasodium tripolyphosphate). Another non-limiting example of a pharmaceutical composition that comprises a particle of the present invention is a pharmaceutical composition comprising a plurality of heteroparticulate particles and at least one pharmaceutical carrier, wherein the heteroparticulate particles comprise: (a) an inner, larger particle comprising an opioid receptor antagonist; and (b) a plurality of outer, smaller particles comprising at least one surfactant and at least one additive, wherein the average diameter of the outer particles is between about 100-500 nm, as that range is described herein. In certain embodiments, the range of the average diameter of the outer particles is greater, such as between about 100-1000 nm.

Methods of making particles comprising an opioid receptor antagonist are also contemplated. For example, certain embodiments of the present invention contemplate a method of making one or more particles wherein each particle comprises an opioid receptor antagonist. The method may comprise, for example: (a) dissolving an opioid receptor antagonist in water to form a dissolved opioid receptor antagonist solution; (b) adding the dissolved opioid receptor antagonist solution to a solution comprising a first additive to form an opioid receptor antagonist/first additive solution;

and (c) adding the opioid receptor antagonist/first additive solution to a solution comprising a second additive, such that the plurality of particles is made. Such methods may further comprise, e.g., stirring of the solution comprising the second additive as the dissolved opioid receptor antagonist/first additive solution is added. In certain embodiments, such methods further comprise (d) centrifuging the suspension such that liquid therein is separated from the particles comprising the opioid receptor antagonist; (e) removing the supernatant; and (e) lyophilizing the particles. Such methods may further comprise encapsulating the particles in an enteric coating. Enteric coatings are described herein. The opioid receptor antagonist may be any opioid receptor antagonist described herein.

As noted herein, a particle of the present invention that comprises an opioid receptor antagonist may be a heteroparticulate particle. The present invention contemplates a heteroparticulate particle comprising: (a) an inner, optionally larger or optionally smaller particle comprising an opioid receptor antagonist; and (b) an outer, optionally smaller or optionally larger particle. The heteroparticulate particle may comprise at least one surfactant and/or at least one additive, as those terms are described herein. The diameter of a heteroparticulate particle may range from 30-1000 nm or higher, as that range is described herein. In certain embodiments, a heteroparticulate particle has a diameter of the outer particle that is between about 100-500 nm, as that range is described herein. In certain embodiments, a heteroparticulate particle has a diameter of the outer particle that is between about 100-1000 nm. The inner, larger particle may be further defined as a microparticle. The inner particle may be a nanoparticle. The inner, larger particle of part (a) may further comprise a loading agent. Loading agents are described herein. A loading agent may comprise, e.g., $SiO_2$. The loading agent may be further defined as, e.g., Aerosil® 200. In certain embodiments, the inner, larger particle comprises a core of the opioid receptor antagonist coated by a plurality of outer particles. In certain embodiments, the outer particles in a heteroparticulate particle comprise an opioid receptor antagonist. In certain embodiments, one or more outer, smaller particles of a heteroparticulate particle is formulated as an enteric coating.

Any particle of the present invention may comprise a surfactant. Surfactants are described herein. For example, a surfactant may comprise a phosphatidylcholine. Phosphatidylcholines are described herein. A surfactant may be, for example, Epikuron 170®. A surfactant may be a nonionic surfactant, such as Tween® 80.

Any particle of the present invention may comprise a time-release agent. Time-release agents are described herein. In certain embodiments, the outer, smaller particle of a heteroparticulate particle is formulated with a time-release agent that permits release of an opioid receptor antagonist over time. Such a time-release agent may be, e.g., a poly(caprolactone).

Another general aspect of the present invention contemplates a heteroparticulate particle comprising: (a) an inner phase comprising one larger particle, wherein the larger particle comprises an opioid receptor antagonist and a loading agent; and (b) an outer phase comprising a plurality of smaller particles, wherein each smaller particle comprises Epikuron 170®, Tween® 80, a poly(caprolactone) polymer and/or a Eudragit® polymer.

Also contemplated are methods of making a heteroparticulate particle comprising an opioid receptor antagonist. Such methods may comprise, for example, (a) preparing an aqueous suspension comprising a plurality of first particles; (b) dispersing at least one second particle comprising an opioid receptor antagonist into the aqueous suspension comprising a plurality of first particles; and (c) spray-drying the product of step (b), wherein the diameter of the second particle is larger than the average diameter of the plurality of first particles. Such methods may further comprise, e.g., concentrating the aqueous suspension comprising a plurality of first particles. The aqueous suspension comprising a plurality of first particles may comprise: (a) at least two surfactants, wherein one surfactant is dissolved in an aqueous solution; (b) at least two additives, and (c) an organic solvent. In certain embodiments, the average diameter of the plurality of outer particles is about 100-500 nm, as that range is described herein. In certain embodiments, the average diameter of the plurality of outer particles is about 100-1000 nm.

Methods of administering particles of the present invention are also contemplated, and such methods are described herein. For example, a method comprising administering a particle comprising an opioid receptor antagonist and at least one additive to a patient, wherein the particle is either (a) a particle having a diameter of about 30-1000 nm, as that range is described herein; or (b) a heteroparticulate particle having an inner particle and an outer particle, wherein the inner particle comprises the opioid receptor antagonist and wherein the diameter of the outer particle is about 100-500 nm, as that range is described herein, is contemplated. In certain embodiments, the diameter of the outer particle is greater, such as between about 100-1000 nm. Any particle of the present invention may be employed in such methods. As discussed herein, such administration may be, e.g., orally, intraadiposally, intraarterially, intraarticularly, intradermally, intralesionally, intramuscularly, intranasally, intraocularally, intraperitoneally, intrapleurally, intrarectally, intrathecally, intratracheally, intraumbilically, intravenously, intravesicularly, intravitreally, liposomally, locally, mucosally, parenterally, rectally, subconjunctival, subcutaneously, sublingually, topically, transbuccally, transdermally, in creams, in lipid compositions, via a catheter, via a lavage, via continuous infusion, via infusion, via inhalation, via injection, via local delivery, via localized perfusion, bathing target cells directly, or any combination thereof. In particular embodiments, the administration is orally, intravenously, or via injection. The outer particles of the heteroparticulate particle may be further defined as a plurality of outer particles. The particle may be formulated to release the opioid receptor antagonist over time.

Patients or subjects of any appropriate method described herein are described below. For example, a patient may be suffering from or may be at risk of suffering from constipation, dysphoria, pruritus, or urinary retention. In certain embodiments, the patient is suffering from or is at risk of suffering a disorder selected from ileus, post-operative ileus, paralytic ileus, post-partum ileus, gastrointestinal dysfunction developing following abdominal surgery, and idiopathic constipation. In certain embodiments, the patient is suffering from a disorder mediated by opioid receptor activity selected from cancer involving angiogenesis, an inflammatory disorder, immune suppression, a cardiovascular disorder, chronic inflammation, chronic pain, sickle cell anemia, a vascular wound, retinopathy, decreased biliary secretion, decreased pancreatic secretion, biliary spasm, and increased gastroesophageal reflux.

In particular embodiments, the present invention contemplates a method comprising administering to a patient a particle comprising at least one opioid receptor antagonist and chitosan.

Other general aspects of the present invention contemplate a method for preventing an opioid-induced side effect in a patient comprising orally administering an effective amount of a particle of the present invention, such as an enterically coated particle, comprising an opioid receptor antagonist and at least one additive to the patient prior to administration of an opioid, wherein, for example, the enterically coated particle is either (a) a particle having a diameter of about 30-1000 nm, as that range is described herein; or (b) a heteroparticulate particle having an inner particle and a plurality of outer particles, wherein the inner particle comprises the opioid receptor antagonist and wherein the outer particles each comprise an enteric agent and the average diameter of the outer particles is about 100-500 nm, as that range is described herein. In certain embodiments, the range of the average diameter of the outer particles is greater, such as between about 100-1000 nm. The opioid induced side effect may comprise, for example, at least one effect selected from inhibition of intestinal motility, gastrointestinal dysfunction, constipation, bowel hypomotility, impaction, gastric hypomotility, inhibition of gastric motility, inhibition of gastric emptying, delayed gastric emptying, incomplete evacuation, nausea, emesis, cutaneous flushing, bloating, abdominal distension, sweating, dysphoria, pruritis, and urinary retention. In certain embodiments, the effective amount of the enterically coated particle comprising an opioid receptor antagonist is less than the effective amount of an aqueous solution of the opioid receptor antagonist. In certain embodiments, the effective amount of the particle, such as an enterically coated particle, comprising an opioid receptor antagonist is less than the effective amount of an enterically coated opioid receptor antagonist that is not comprised in an enterically coated particle. In certain embodiments, the effective amount of the enterically coated opioid receptor antagonist that is not comprised in a particle is further defined as either: (a) an effective amount of an enterically coated opioid receptor antagonist that is not comprised in a particle having a size of about 30-1000 nm, as that range is described herein; or (b) an effective amount of an enterically coated opioid receptor antagonist that is not comprised in a heteroparticulate particle having an inner particle and a plurality of outer particles, wherein the inner particle comprises the opioid receptor antagonist and wherein the outer particles each comprise an enteric agent and the average diameter of the outer particles is about 100-500 nm. In certain embodiments, the range of the average diameter of the outer particles is greater, such as between about 100-1000 nm.

Dosages of particles of the present invention are described herein. In certain embodiments of any method described herein, the dosage of a particle comprising an opioid receptor antagonist, such as an enterically coated particle, is about 0.1-10 mg/kg body weight, as that range is described herein.

Also contemplated are methods for treating an opioid induced side effect comprising administering, e.g., orally administering, an effective amount of a particle, such as an enterically coated particle, comprising an opioid receptor antagonist to a patient subsequent to administration of an opioid. The particle may be, for example, either (a) a particle having a diameter of about 30-1000 nm, as that range is described herein; or (b) a heteroparticulate particle having an inner particle and a plurality of outer particles, wherein the inner particle comprises the opioid receptor antagonist and wherein the outer particles each comprise an enteric agent and the average diameter of the outer particles is about 100-500 nm, as that range is described herein. In certain embodiments, the range of the average diameter of the outer particles is greater, such as between about 100-1000 nm. In certain embodiments, the effective amount of the enterically coated particle comprising an opioid receptor antagonist is less than the effective amount of an aqueous solution of the opioid receptor antagonist. In certain embodiments, the effective amount of the enterically coated particle comprising an opioid receptor antagonist is less than the effective amount of an enterically coated opioid receptor antagonist that is not comprised in a particle.

Methods for treating gastrointestinal dysfunction following abdominal surgery comprising administering a particle of the present invention to a patient are contemplated, such as methods comprising orally administering an effective amount of an enterically coated particle comprising an opioid receptor antagonist to a patient, wherein the dysfunction is treated, wherein the particle is either: (a) a particle having a diameter of about 30-1000 nm, as that range is described herein; or (b) a heteroparticulate particle having an inner particle and a plurality of outer particles, wherein the inner particle comprises the opioid receptor antagonist and wherein the outer particles each comprise an enteric agent and the average diameter of the outer particles is about 100-500 nm, as that range is described herein. In certain embodiments, the range of the average diameter of the outer particles is greater, such as between about 100-1000 nm.

Methods for preventing inhibition of gastrointestinal motility in a patient are also contemplated, such as methods for preventing inhibition of gastrointestinal motility in a patient prior to the patient receiving an opioid for pain resulting from surgery comprising administering an effective amount of a particle of the present invention, such as an enterically coated particle, comprising an opioid receptor antagonist to the patient, wherein the particle is either (a) a particle having a diameter of about 30-1000 nm, as that range is described herein; or (b) a heteroparticulate particle having an inner particle and a plurality of outer particles, wherein the inner particle comprises the opioid receptor antagonist and wherein the outer particles each comprise an enteric agent and the average diameter of the outer particles is about 100-500 nm, as that range is described herein. In certain embodiments, the range of the average diameter of the outer particles is greater, such as between about 100-1000 nm.

Another general aspect of the present invention contemplates a method for treating inhibition of gastrointestinal motility in a patient receiving an opioid for pain resulting from surgery comprising administering an effective amount of a particle of the present invention, such as an enterically coated particle, comprising an opioid receptor antagonist to the patient. The particle may be, for example, either: (a) a particle having a diameter of about 30-1000 nm, as that range is described herein; or (b) a heteroparticulate particle having an inner particle and a plurality of outer particles, wherein the inner particle comprises the opioid receptor antagonist and wherein the outer particles each comprise an enteric agent and the average diameter of the outer particles is about 100-500 nm, as that range is described herein. In certain embodiments, the range of the average diameter of the outer particles is greater, such as between about 100-1000 nm.

Also contemplated are methods of preventing or treating an opioid-induced side effect in a chronic opioid patient, comprising administering an effective amount of a particle of the present invention, such as an enterically coated particle comprising an opioid receptor antagonist, to the patient. The particle may be, for example, either: (a) a particle having a diameter of about 30-1000 nm, as that range is described herein; or (b) a heteroparticulate particle having an inner particle and a plurality of outer particles, wherein the inner particle comprises the opioid receptor antagonist and wherein the outer particles each comprise an enteric agent and the average diameter of the outer particles is about 100-500 nm, as that range is described herein. The side effect may be, for example, inhibition of intestinal motility, gastrointestinal dysfunction, constipation, bowel hypomotility, impaction, gastric hypomotility, inhibition of gastric motility, inhibition of gastric emptying, delayed gastric emptying, incomplete evacuation, nausea, emesis, cutaneous flushing, bloating, abdominal distension, sweating, dysphoria, pruritis, or urinary retention.

In certain embodiments, following administration of a particle comprising an opioid receptor antagonist, the opioid receptor antagonist is not substantially released in the stomach. As used herein, "the opioid receptor antagonist is not substantially released in the stomach" refers to a method wherein less than 10% of the administered opioid receptor antagonist is released in the stomach. The reduced drug absorption by the stomach may be measured using any technique known in the art, such as by drug plasma level analysis using, e.g., HPLC, such as $C_{max}$, $T_{max}$, and AUC (area under the curve). See, e.g., Yuan et al., 1997 and Yuan et al., 2000.

Any embodiment discussed with respect to one aspect of the invention applies to other aspects of the invention as well.

The embodiments in the Example section are understood to be embodiments of the invention that are applicable to all aspects of the invention.

The term "effective," as that term is used in the specification and/or claims, means adequate to accomplish a desired, expected, or intended result.

"Therapeutically effective amount" means that amount which, when administered to a subject for treating a condition, disease, or side effect, is sufficient to effect such treatment for the condition, disease, or side effect.

"Treatment" or "treating" includes: (1) inhibiting a condition, disease, or side effect in a subject or patient experiencing or displaying the pathology or symptomatology of the condition, disease, or side effect (e.g., arresting further development of the pathology and/or symptomatology), (2) ameliorating a condition, disease, or side effect in a subject or patient that is experiencing or displaying the pathology or symptomatology of the condition, disease, or side effect (e.g., reversing the pathology and/or symptomatology), and/or (3) effecting any measurable decrease in a condition, disease, or side effect in a subject or patient that is experiencing or displaying the pathology or symptomatology of the condition, disease, or side effect.

"Prevention" or "preventing" includes: (1) inhibiting the onset of a condition, disease, or side effect in a subject or patient who may be at risk and/or predisposed to the condition, disease, or side effect but does not yet experience or display any or all of the pathology or symptomatology of the condition, disease, or side effect, and/or (2) slowing the onset of the pathology or symptomatology of the condition, disease, or side effect in a subject or patient which may be at risk and/or predisposed to the condition, disease, or side effect but does not yet experience or display any or all of the pathology or symptomatology of the condition, disease, or side effect.

As used herein, the term "patient" or "subject" refers to a living mammalian organism, such as a human, monkey, cow, sheep, goat, dog, cat, mouse, rat, guinea pig, or transgenic species thereof. Non-limiting examples of human subjects are adults, juveniles, children, infants and fetuses.

In certain embodiments, a patient is a chronic opioid user. Accordingly, aspects of the invention are useful to prevent or reduce the occurrence or reoccurrence of an opioid-induced side effect in a chronic opioid patient. A chronic opioid patient may be any of the following: a cancer patient, an AIDS patient, or any other terminally ill patient. A chronic opioid patient may be a patient taking methadone. Chronic opioid use is characterized by the need for substantially higher levels of opioid to produce the therapeutic benefit as a result of prior opioid use, as is well known in the art. Chronic opioid use is also characterized by the need for substantially lower levels of opioid antagonist to produce the therapeutic benefit. Chronic opioid use as used herein includes daily opioid treatment for a week or more or intermittent opioid use for at least two weeks. In one embodiment, a patient, such as a chronic opioid user, is taking a laxative and/or a stool softener.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Accordingly, pharmaceutically acceptable salts of compounds of the present invention are contemplated herein. Such pharmaceutically acceptable salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (P. H. Stahl & C. G. Wermuth eds., Verlag Helvetica Chimica Acta, 2002), which is incorporated herein by reference.

It is contemplated that any embodiment discussed in this specification can be implemented with respect to any method or composition of the invention, and vice versa. Furthermore, compositions of the invention can be used to achieve methods of the invention.

It is also contemplated that any method described herein may be described using Swiss-type use language.

The use of the term "or" in the claims is used to mean "and/or" unless explicitly indicated to refer to alternatives only or the alternatives are mutually exclusive.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

The Figure shows methylnaltrexone (MNTX) plasma levels at the indicated times after oral administration of MNTX, N1-MNTX, and N2-MNTX to rats.

DESCRIPTION OF ILLUSTRATIVE EMBODIMENTS

I. Opioid Receptor Antagonists

The opioid receptor antagonists of the present invention include both centrally and peripherally acting opioid receptor antagonists. In certain embodiments, peripherally acting opioid receptor antagonists are contemplated.

Opioid receptor antagonists form a class of compounds that can vary in structure while maintaining their antagonist properties. These compounds include tertiary and quaternary morphinans, such as noroxymorphone derivatives; N-substituted piperidines, such as piperidine-N-alkylcarboxylates, tertiary and quaternary benzomorphans, and tertiary and quaternary normorphinan derivatives, such as 6-carboxynormorphinan derivatives. Tertiary compound antagonists are fairly lipid soluble and cross the blood-brain barrier easily. Examples of opioid receptor antagonists that cross the blood-brain barrier and are centrally (and peripherally) active include, e.g., naloxone, naltrexone (each of which is commercially available from Baxter Pharmaceutical Products, Inc.), and nalmefene (available, e.g., from DuPont Pharma). Peripherally restricted antagonists, on the other hand, are typically charged, polar, and/or of high molecular weight: these properties typically impede their crossing the blood-brain barrier. Methylnaltrexone is a quaternary derivative of the tertiary opioid receptor antagonist, naltrexone. Addition of the methyl group to naltrexone forms a compound with greater polarity and lower lipid solubility. Thus, methylnaltrexone does not cross the blood-brain barrier and has the potential for blocking the undesired adverse effects which are typically mediated by peripherally located receptors.

A peripheral opioid receptor antagonist suitable for use in the invention may be a compound which is a quaternary morphinan derivative, such as a quaternary noroxymorphone of formula (I):

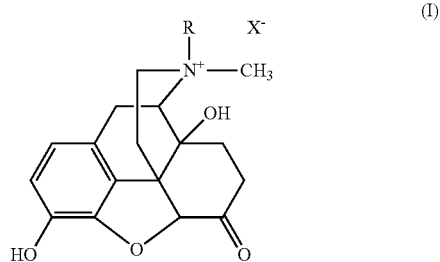

wherein R is alkyl, alkenyl, alkynyl, aryl, cycloalkyl-substituted alkyl, or arylsubstituted alkyl, and $X^-$ is the anion, such as a chloride, bromide, iodide, or methylsulfate anion. The noroxymorphone derivatives of formula (I) can be prepared, for example, according to the procedure in U.S. Pat. No. 4,176,186, which is incorporated herein by reference; see also U.S. Pat. Nos. 4,719,215; 4,861,781; 5,102,887; 5,972,954; and 6,274,591; U.S. Patent Application Nos. 2002/0028825 and 2003/0022909; and PCT publication Nos. WO 99/22737 and WO 98/25613, all of which are hereby incorporated by reference.

A compound of formula (I) may be N-methylnaltrexone (or simply methylnaltrexone), wherein R is cyclopropylmethyl as represented in formula (II):

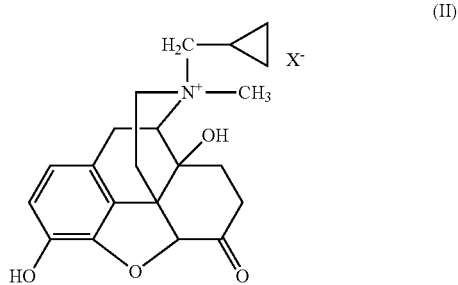

wherein $X^-$ may be any pharmaceutically acceptable anion. Methylnaltrexone is a quaternary derivative of the μ-opioid receptor antagonist naltrexone. Methylnaltrexone exists as a salt (e.g., N-methylnaltrexone bromide) and the terms "methylnaltrexone" or "MNTX", as used herein, therefore embrace such salts. "Methylnaltrexone" or "MNTX" thus specifically includes, but is not limited to, bromide salts, chloride salts, iodide salts, carbonate salts, and sulfate salts of methylnaltrexone. Names used for the bromide salt of MNTX in the literature, for example, include: methylnaltrexone bromide; N-methylnaltrexone bromide; naltrexone methobromide; naltrexone methyl bromide; SC-37359; MRZ-2663-BR; and N-cyclopropylmethylnoroxy-morphine-methobromide. A compound of formula (I) may be S—N-methylnaltrexone.

Methylnaltrexone is commercially available from, e.g., Mallinckrodt Pharmaceuticals, St. Louis, Mo. Methylnaltrexone is provided as a white crystalline powder, freely soluble in water, typically as the bromide salt. The compound as provided is 99.4% pure by reverse phase HPLC, and contains less than 0.011% unquaternized naltrexone by the same method. Methylnaltrexone can be prepared as a sterile solution at a concentration of, e.g., about 5 mg/Ml Other suitable peripheral opioid receptor antagonists may include N-substituted piperidines, such as piperidine-N-alkylcarboxylates as represented by formula (III):

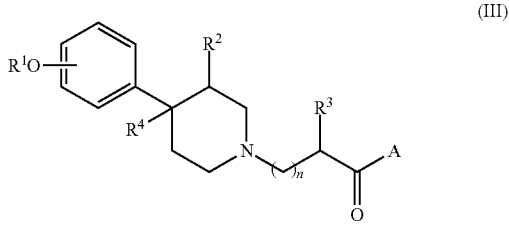

(III)

wherein $R^1$ is hydrogen or alkyl; $R^2$ is hydrogen, alkyl, or alkenyl; $R^3$ is hydrogen, alkyl, alkenyl, aryl, cycloalkyl, cycloalkenyl, cycloalkyl-substituted alkyl, cycloalkenyl-substituted alkyl, or aryl-substituted alkyl; $R^4$ is hydrogen, alkyl, or alkenyl; A is $OR^5$ or $NR^6R^7$; wherein $R^5$ is hydrogen, alkyl, alkenyl, cycloalkyl, cycloalkenyl, cycloalkyl-substituted alkyl, cycloalkenyl-substituted alkyl, or aryl-substituted alkyl; $R^6$ is hydrogen or alkyl; $R^7$ is hydrogen, alkyl, alkenyl, aryl, cycloalkyl, cycloalkenyl, cycloalkyl-substituted alkyl, cycloalkenyl-substituted alkyl or aryl-substituted alkyl, or alkylene-substituted B or together with the nitrogen atom to which they are attached, $R^6$ and $R^7$ form a heterocyclic ring selected from pyrrole and piperidine; B is

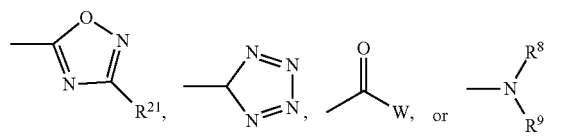

wherein $R^8$ is hydrogen or alkyl; $R^9$ is hydrogen, alkyl, alkenyl, aryl, cycloalkyl, cycloalkenyl, cycloalkyl-substituted alkyl, cycloalkenyl-substituted alkyl or aryl-substituted alkyl or together with the nitrogen atom to which they are attached, $R^8$ and $R^9$ form a heterocyclic ring selected from pyrrole and piperidine; W is $OR^{10}$, $NR^{11}R^{12}$, or OE; wherein $R^{10}$ is hydrogen, alkyl, alkenyl, cycloalkyl, cycloalkenyl, cycloalkyl-substituted alkyl, cycloalkenyl-substituted alkyl, or aryl-substituted alkyl; $R^{11}$ is hydrogen or alkyl; $R^{12}$ is hydrogen, alkyl, alkenyl, aryl, cycloalkyl, cycloalkenyl, cycloalkyl-substituted alkyl, cycloalkenyl-substituted alkyl, aryl-substituted alkyl, or alkylene-substituted C(=O)Y or, together with the nitrogen atom to which they are attached, $R^{11}$ and $R^{12}$ form a heterocyclic ring selected from pyrrole and piperidine; E is

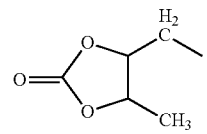

alkylene-substituted (C=O)D, or $-R^{13}OC(=O)R^{14}$; wherein $R^{13}$ is alkyl-substituted alkylene; $R^{14}$ is alkyl; D is $OR^{15}$ or $NR^{16}R^{17}$; wherein $R^{15}$ is hydrogen, alkyl, alkenyl, cycloalkyl, cycloalkenyl, cycloalkyl-substituted alkyl, cycloalkenyl substituted alkyl, or aryl-substituted alkyl; $R^{16}$ is hydrogen, alkyl, alkenyl, aryl, aryl-substituted alkyl, cycloalkyl, cycloalkenyl, cycloalkyl substituted alkyl, or cycloalkenyl-substituted alkyl; $R^{17}$ is hydrogen or alkyl or, together with the nitrogen atom to which they are attached, $R^{16}$ and $R^{17}$ form a heterocyclic ring selected from the group consisting of pyrrole or piperidine; Y is $OR^{18}$ or $NR^{19}R^{20}$; wherein $R^{18}$ is hydrogen, alkyl, alkenyl, cycloalkyl, cycloalkenyl, cycloalkyl-substituted alkyl, cycloalkenyl-substituted alkyl, or aryl-substituted alkyl; $R^{19}$ is hydrogen or alkyl; $R^{20}$ is hydrogen, alkyl, alkenyl, aryl, cycloalkyl, cycloalkenyl, cycloalkyl-substituted alkyl, cycloalkenyl-substituted alkyl, or aryl-substituted alkyl or, together with the nitrogen atom to which they are attached, $R^{19}$ and $R^{20}$ form a heterocyclic ring selected from pyrrole and piperidine; $R^{21}$ is hydrogen or alkyl; and n is 0 to 4.

Non-limiting examples of suitable N-substituted piperidines may be prepared as disclosed in U.S. Pat. Nos. 5,270,328; 6,451,806; and 6,469,030, all of which are hereby incorporated by reference. Such compounds have moderately high molecular weights, a zwitterionic form, and a polarity that prevent penetration of the blood-brain barrier.

Particular piperidine-N-alkylcarbonylates include N-alkylamino-3,4,4-substituted piperidines, such as alvimopan represented below as formula (IV):

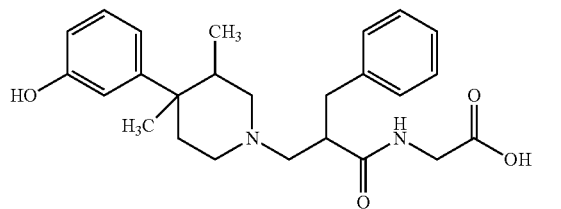

(IV)

Alvimopan is available from Adolor Corp., Exton, Pa.

Still other suitable peripheral opioid receptor antagonist compounds may include quaternary benzomorphan compounds. Quaternary benzomorphan compounds may have the following formula (V):

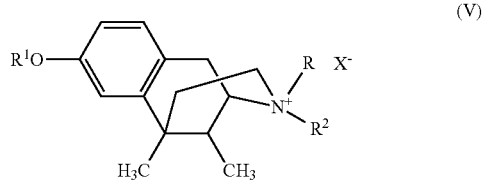

(V)

wherein R[1] is hydrogen, acyl, or acetoxy; and R[2] is alkyl or alkenyl; R is alkyl, alkenyl, or alkynyl and X[−] is an anion, such as a chloride, bromide, iodide, or methylsulfate anion.

Specific quaternary derivatives of benzomorphan compounds that may be employed in the methods of the invention include the following compounds of formula (V): 2'-hydroxy-5,9-dimethyl-2,2-diallyl-6,7-benzomorphanium-bromide; 2'-hydroxy-5,9-dimethyl-2-n-propyl-2-allyl-6,7-benzomorphanium-bromide; 2'-hydroxy-5,9-dimethyl-2-n-propyl-2-propargyl-6,7-benzomorphanium-bromide; and 2'-acetoxy-5,9-dimethyl-2-n-propyl-2-allyl-6,7-benzomorphanium-bromide.

Other quaternary benzomorphan compounds that may be employed in methods of the invention are described, for example, in U.S. Pat. No. 3,723,440, the entire disclosure of which is incorporated herein by reference.

Other peripheral opioid antagonists include 6-carboxynormorphinan derivatives, particularly N-methyl-C-normorphinan derivatives, as described in U.S. Published Application No. 2008/0064744, hereby incorporated in its entirety herein by reference, and including the compound having the following formula (VI):

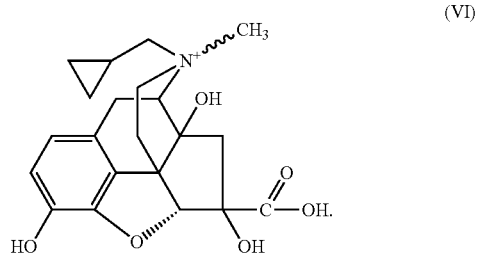

(VI)

Other peripheral opioid antagonists may include polymer conjugates of opioid antagonists, as described in U.S. Published Application No. 2006/0105046, hereby incorporated by reference. Specific polymer conjugates include PEGylated naloxone and naltrexone.

The invention also encompasses administration of more than one opioid receptor antagonist. Any combination of opioid receptor antagonists is contemplated, including combinations of μ-opioid receptor antagonists and combinations of μ- and κ-antagonists: for example, a combination of methylnaltrexone and alvimopan.

II. Particles of the Present Invention

Particles of the present invention comprise at least one opioid receptor antagonist. Certain properties of particles of the present invention are discussed below.

A. Properties of Particles

As noted above, a particle may comprise only one type of particle ("homoparticulate"), or a particle may comprise two or more types of particles ("heteroparticulate"). Accordingly, the term "particle" encompasses both homo- and heteroparticulate particles. A "type" of particle refers to a particle comprising a particular set of ingredients. Thus, two different types of particles will have two different sets of ingredients (e.g., one particle comprises an opioid receptor antagonist and one particle does not). If two particles contain the same ingredients but the ratio of ingredients differs, the two particles are still considered to be of the same "type."

A particle may comprise two or more particles and still be a homoparticulate particle, wherein the two or more particles are of the same type. For example, if a particle comprises two particles having different sizes, but the ingredients of each particle is the same, then the particle is a homoparticulate particle. If a particle comprises two or more particles and the two or more particles are of different types, then the particle is a heteroparticulate particle regardless of the sizes of the particles. In any case, the two or more particles may be in physical contact with each other such that the particles are found together as a unit, wherein that unit is also considered a particle.

In certain embodiments, a particle may comprise a single particle. In certain embodiments, a particle may comprise two or more particles. Accordingly, the term "particle" encompasses particles having only one particle, and particles having two or more particles. Regarding particles comprising two or more particles, there may be an inner particle and an outer particle. For example, an inner particle may be in physical contact with one or more particles that are found on the surface of the inner particle such that they are "outer" particles. In certain embodiments, a plurality of outer particles coat the inner particle. As used herein, "coat" refers to where a plurality of outer particles are found on about, at most about, or at least about 90% of the surface of the inner particle. In certain embodiments, "coat" refers to where a plurality of outer particles are found on about, at most about, or at least about 90%, 95%, 99%, or more, of the surface of the inner particle, or any range derivable therein.

Generally speaking, then, any particle may be either a homoparticulate particle or a heteroparticulate particle; any particle may comprise only one particle, wherein that particle may be either a homoparticulate particle or a heteroparticulate particle; or any particle may comprise two or more particles, wherein each of the two or more particles may be homoparticulate particles or heteroparticulate particles, or a combination thereof.

The following schematic demonstrates non-limiting representations of cross-sections of particles of the present invention, wherein each individual circle represents a particle, and each of A-S represents a particle, and each particle may be the same type or may be different types. These representations are not to scale and are merely for illustrative purposes. The particles are not necessarily spherical.

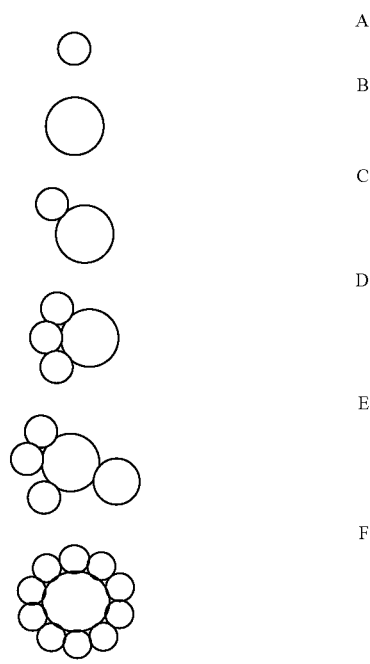

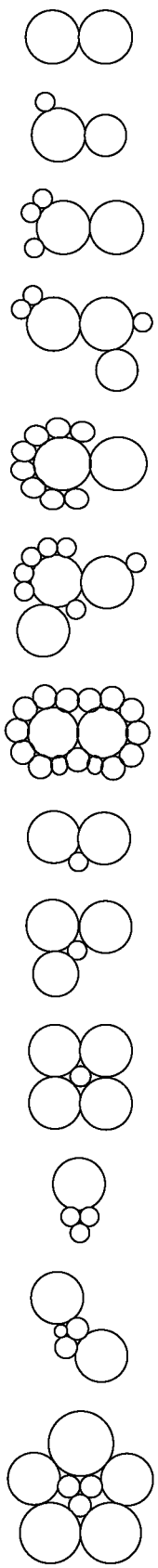

The diameters discussed herein apply to any type of particle described herein, unless specifically noted otherwise. For example, a homoparticulate particle, a heteroparticulate particle, or the particles that make up a homoparticulate particle or a heteroparticulate particle may each have a diameter as discussed herein or, in the case of a plurality of particles, the plurality may have an average diameter of the values discussed herein. Any plurality of particles, as used herein, may all have about the same size diameter, or may together have an average diameter size.

In certain embodiments, the diameter of a particle of the present invention (or the average diameter of a plurality of particles) is about 30-1000 nm. In certain embodiments, the diameter is about, at most about, or at least about 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990 or 1000 nm or higher, or any range derivable therein. In certain embodiments, a particle's diameter is less than 300 µm, or less than about 300 µm. In certain embodiments, a diameter is less than, or less than about 300, 275, 250, 200, 150, 100, 75, 50, 10, 1, 0.75, 0.50, 0.25, 0.1, 0.01, or 0.001 µm, or any range derivable therein. In certain embodiments, a particle's diameter is less than 300 µm, or less than about 300 µm, and greater than 1 nm (e.g., less than, or less than about 300, 200, 100, 75, 50, 25, 10, 1, 0.1, or 0.010 µm and greater than about 1 nm, or any range derivable therein). When a plurality of such particles is employed, the average diameter of the plurality of particles may be any of the values discussed in this paragraph.

In certain embodiments, a particle may comprise an outer particle that is found on the surface of an inner particle. Typically, a plurality of outer particles are found on the surface and in some embodiments, a plurality of outer particles coat an individual inner particle. In certain embodiments, the inner and outer particles comprise the same ingredients, such that the particle is a homoparticulate particle. In certain embodiments, the inner particle comprises different ingredients than the outer particle, such that the particle is a heteroparticulate particle. In certain embodiments, the inner and/or outer particle(s) is further defined as a microparticle or a nanoparticle (defined below). In certain embodiments, a particle may comprise a smaller, outer particle that is found on the surface of an individual larger, inner particle and typically, a plurality of smaller particles coat the individual larger, inner particle. In certain embodiments, the diameter of the outer particle ranges from about, at most about, or at least about 100-500 nm. For example, the diameter of the outer particle may be about, at least about, or at most about 100, 125, 150, 175, 200, 225, 250, 275, 300, 325, 350, 375, 400, 425, 450, 475, 500 nm, or any range derivable therein. In other embodiments, the range of the diameter of the outer particle may be larger, such as about, at least about, or at most about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975 or 1000 nm, or any range derivable therein. In certain embodiments wherein a plurality of outer, smaller particles coat an inner, larger particle, the average diameter of the plurality of outer, smaller particles ranges between about 100-500 nm, as this range is described above. In certain embodiments, a larger, outer particle is found on the surface of an individual smaller, inner particle. In certain embodiments, a plurality of larger particles are found on the surface of an individual smaller, inner particle. In certain embodiments, a plurality of larger particles coat the surface of an individual inner, smaller particle, wherein the meaning of "coat" is as described above.

In certain embodiments, particles of the present invention are microparticles. A microparticle is defined as a particle having a diameter of about 0.1-100 μm. In certain embodiments, the diameter of a microparticle is about 0.1, 0.2, 0.3, 0.4, 0.5, 0.6, 0.7. 0.8, 0.9, 1, 1.5, 2, 5, 10, 15, 20, 25, 30, 35, 40, 45, 50, 55, 60, 65, 70, 75, 80, 85, 90, 95 or 100 μm, or any range derivable therein. In certain embodiments, a particle comprises only one microparticle. In certain embodiments, a particle comprises or contains only a plurality of microparticles. In certain embodiments, a microparticle may be comprised in a homoparticulate particle. In certain embodiments, a microparticle may be comprised in a heteroparticulate particle. In certain embodiments, at least one particle having a smaller diameter than the microparticle is found on the surface of the microparticle. In certain embodiments, a plurality of smaller, outer particles coat the microparticle. In certain embodiments, one or more larger, outer particles coat the microparticle.

In certain embodiments, particles of the present invention are nanoparticles. A nanoparticle is defined as a particle having a diameter of about 1-100 nm. In certain embodiments, the diameter of a nanoparticle is about 1, 2, 5, 10, 15, 20, 25, 30, 35, 40, 45, 50, 55, 60, 65, 70, 75, 80, 85, 90, 95 or 100 nm, or any range derivable therein. In certain embodiments, a particle comprises only one nanoparticle. In certain embodiments, a particle comprises or contains only a plurality of nanoparticles. In certain embodiments, a nanoparticle may be comprised in a homoparticulate particle. In certain embodiments, a nanoparticle may be comprised in a heteroparticulate particle. In certain embodiments, a plurality of nanoparticles coat an inner particle. In certain embodiments, a plurality of smaller, outer nanoparticles coat a larger, inner particle. In certain embodiments, the inner particle of a homo- or heteroparticulate particle is a nanoparticle; further, in certain embodiments, one or more larger or smaller particles may be found on the surface of such a nanoparticle. For example, a plurality of larger or smaller particles may coat the surface of a nanoparticle.

Particle diameters may also span the diameters described for micro- and nanoparticles (e.g., about 30-1000 nm, as that range is described herein).

B. Additives

A variety of additives may be employed in the particles of the present invention. Additives may be characterized in more than one fashion. In certain embodiments polymeric additives may be employed. In certain embodiments, polysaccharides may be employed. Homopolysaccharides and/or heteropolysaccharides are contemplated, as well as a variety of molecular weights (e.g., 10,000-150,000 g/mol). Non-limiting examples of polysaccharides include chitosan and cellulose (e.g., microcrystalline cellulose). Hydrophobic additives may be employed, in certain embodiments. A hydrophobic additive is defined as an additive having a surface energy that is less than 40 dynes/cm. Non-limiting examples of hydrophobic additives include methacrylic acid copolymer, sodium carboxymethyl cellulose, cellulose acetate, ethyl cellulose (EC), hydroxypropyl methyl-cellulose acetate succinate (HPMCAS) and cellulose acetate phthalate (CAP). Hydrophilic additives are also contemplated, in certain embodiments. A hydrophilic additive is defined as an additive having a surface energy of ≥40 dynes/cm. Certain hydrophilic additives are positively charged at acidic and neutral pH, and certain hydrophilic additives are negatively charged at acidic and neutral pH. Non-limiting examples of hydrophilic additives include, for example, chitosan and/or polyphosphates such as tripolyphosphate (e.g., pentasodium tripolyphosphate, TPP). Hydrophilic additives may also be either polycationic and/or polyanionic. An example of a polyanionic additive is a polyphosphate, such as TPP. Yet another example of a polyanionic additive is dextran sulfate (Sarmento et al., 2007).

When more than one additive is present in a particle, the ratio of the additives in the particle may vary widely. For example, the ratio of one additive to any other additive in a particle may range from 1:1 to 1:100,000 w/w. In certain embodiments, the w/w ratio is 1:1, 1:1.5, 1:2, 1:2.5, 1:3, 1:4, 1:5, 1:6, 1:7, 1:8, 1:9, 1:10, 1:25, 1:50, 1:100, 1:250, 1:500, 1:750, 1:1000, 1:1500, 1:2000, 1:2500, 1:3000, 1:3500, 1:4000, 1:4500, 1:5000, 1:5500, 1:6000, 1:6500, 1:7000, 1:7500, 1:8000; 1:8500; 1:9000, 1:9500, 1:10,000, 1:25,000, 1:50,000, 1:75,000 or 1:100,000, or any range derivable therein. In certain embodiments, the ratio is 1:1. In certain embodiments, the ratio is 1:10 w/w. For example, where two additives are present in a particle, the ratio between the two additives may range from 1:1 to 1:100,000, or any range derivable therein, as that range is described above. Where three additives are present, A, B and C, the w/w/w ratios of A:B:C may range from 1:1:1 to 1:100,000:1 to 1:100,000: 100,000 to 100,000:1:1, to 100,000:100,000:1 to 100,000: 1:100,000, to 1:1:100,000, or any range derivable therein, as that range is described above. In certain embodiments, the ratio is 1:1:10 w/w/w. When four or more additives are comprised within a particle of the present invention, the ratios may be adjusted similarly.

Further, when more than one additive is present in a particle, any combination of additives discussed herein may be employed. For example, a polysaccharide and a hydrophobic additive may be employed. A polysaccharide and a hydrophilic additive may be employed. A hydrophobic additive and a hydrophilic additive may be employed. A polycationic and/or a polyanionic additive may be combined with each other or with any other additive described herein. The ratios of these additives may be any ratio as described herein. Further, an additive may be combined with one or more surfactants, enteric agents, time-release agents, or loading agents, as described herein.

The ratio of additive to opioid receptor antagonist may also vary widely. For example, the ratio may range from 9:4 to 9:32 additive:antagonist (w/w). The range may be broader, such as from 9:1 to 9:128 w/w. In certain embodiments, the w/w ratio is 1.8:3.2.

Surfactants may also be employed in certain particles of the present invention. Surfactants are well-known in the art. Non-limiting examples of surfactants include nonionic, cationic and anionic surfactants. In particular embodiments, nonionic surfactants are contemplated, such as Tween® 80. Other nonionic Tween® products are also contemplated. In certain embodiments, phosphatidylcholine surfactants may be employed, such as Epikuron 170®. Phosphatidylcholines, including those obtained from egg, soy beans, or other plant sources or those that are partially or wholly synthetic, or of variable lipid chain length and unsaturation, are suitable for use in the present invention. Synthetic, semi-synthetic and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), dioleoylphosphatidylcholine (DOPC), hydrogenated egg phosphatidylcholine (HEPC), dielaidoylphosphatidylcholine (DEPC), dipalmitoylphosphatidylcholine (DPPC) and dimyristoylphosphatidylcholine (DMPC) are suitable phosphatidylcholines for use in this invention. All of these agents are commercially available. Combinations of surfactants may also be used. Moreover, any surfactant discussed herein may be combined with any one or more additive, polymer, or enteric, time-release, or loading agent, as discussed throughout this application.

C. Enteric, Time-Release and Loading Agents

Any particle of the present invention may be enterically coated. Enteric coatings prevent or inhibit release of medication before the medication reaches the small intestine. In particular, enteric coatings preferentially dissolve in conditions having a higher pH than the acidic pH of the stomach, which typically has a pH of less than about 3.0 (e.g., less than about 3.0, 2.5, 2.0, 1.5, or 1, or any range derivable therein). For example, an enteric coating may dissolve or partially dissolve in a pH of about 3.5, 4.0, 4.5, 5.0, 5.5, 6.0, 6.5, 7.0, 7.5, 8.0, 8.5 or higher, or any range derivable therein.

Agents for enteric coatings are well-known in the art, and include methacrylic acid copolymers, cellulose acetate, styrol maleic acid copolymers, hydroxypropylmethyl cellulose acetate and shellac. Other polymers that may be used for enteric coating purposes include Eudragits®, such as anionic Eudragit® copolymers (e.g., Eudragit® L100 and Eudragit® S100). Enteric coatings may also comprise other agents, such as an acetylated monoglyceride, such as Myvacet® distilled acetylated monoglyceride (e.g., Myvacet 5-07, 7-07, 9-08 and 9-45). Combinations of any enteric agents known in the art, including those described below, are also contemplated. Enteric agents may be combined with one or more additives, polymers, surfactants, time-release agents, and/or loading agents, as described herein. An enteric coating need not coat the entire particle of an enterically coated particle: in certain embodiments, an enteric coating coats at least about 90%, 95%, 99% or 100% of the particle. In certain embodiments, an enteric coating coats 100% of the particle.

Suitable enteric coatings are also described, for example, in U.S. Pat. Nos. 4,311,833; 4,377,568; 4,457,907; 4,462,839; 4,518,433; 4,556,552; 4,606,909; 4,615,885; 4,670,287; 5,536,507; 5,567,423; 5,591,433; 5,597,564; 5,609,871; 5,614,222; 5,626,875; and 5,629,001, all of which are incorporated herein by reference.

Other exemplary enteric agents include alkyl and hydroxyalkyl celluloses and their aliphatic esters, e.g., methylcellulose, ethylcellulose, hydroxyethylcellulose, hydroxypropylcellulose, hydroxybutylcellulose, hydroxyethylethylcellulose, hydroxyprophymethylcellulose, hydroxybutylmethylcellulose, hydroxypropylcellulose phthalate, hydroxypropylmethylcellulose phthalate and hydroxypropylmethylcellulose acetate succinate; carboxyalkylcelluloses and their salts, e.g., carboxymethylethylcellulose; cellulose acetate phthalate; cellulose acetate trimellitate, polycarboxymethylene and its salts and derivatives; polyvinyl alcohol and its esters (e.g., polyvinyl acetate phthalate); polycarboxymethylene copolymer with sodium formaldehyde carboxylate; acrylic polymers and copolymers, e.g., methacrylic acid-methyl methacrylic acid copolymer and methacrylic acid-methyl acrylate copolymer; edible oils such as peanut oil, palm oil, olive oil and hydrogenated vegetable oils; polyvinylpyrrolidone; polyethylene glycol and its esters; and natural products such as shellac, and zein.

Other enteric agents include polyvinylacetate esters, e.g., polyvinyl acetate phthalate; alkyleneglycolether esters of copolymers such as partial ethylene glycol monomethylether ester of ethylacrylate-maleic anhydride copolymer or diethyleneglycol monomethylether ester of methylacrylate-maleic anhydride copolymer, N-butylacrylate-maleic anhydride copolymer, isobutylacrylate-maleic anhydride copolymer or ethylacrylate-maleic anhydride copolymer; and polypeptides resistant to degradation in the gastric environment, e.g., polyarginine and polylysine. Other suitable agents and methods to make and use such formulations are well known to those skilled in the art (see, e.g., Remington: The Science and Practice of Pharmacy, 19th ed. (1995) Mack Publishing Company, Easton, Pa.; herein incorporated by reference).

Certain particles of the present invention may be formulated for time-release of an opioid receptor antagonist. Time-release agents are well-known in the art, and such formulations may comprise an additive, a polymer and/or an enteric agent, surfactant, or loading agent. For example, poly(caprolactone) of a variety of molecular weights (e.g., 30,000-90,000 g/mol) may be employed for this purpose. Non-polymers may also be used, such as tamsulosin, as described in U.S. Published Application No. 2008/0113030, incorporated herein by reference. Combinations of time-release agents are also contemplated.

Loading agents may be employed to facilitate the making of particles. For example, an opioid receptor antagonist may be combined with a loading agent to produce a particle comprising the antagonist and the loading agent, such that the particle is "loaded" with the antagonist. Loading agents suitable for this purpose are well-known in the art. For example, loading agents comprising silica ($SiO_2$) may be employed. Loading agents comprising alkyl$_{(C \leq 5)}$-modified silica may also be used. Such products are commercially available. Combinations of loading agents are also contemplated. Moreover, loading agents may be combined with one or more additives, polymers, surfactants, enteric agents, or time-release agents.

III. Chemical Definitions

"Alkyl" refers to a univalent aliphatic hydrocarbon group which is saturated and which may be straight, branched, or cyclic having from 1 to about 10 carbon atoms in the chain, and all combinations and subcombinations of chains therein. Exemplary alkyl groups include, but are not limited to, methyl, ethyl, n-propyl, isopropyl, butyl, isobutyl, sec-butyl, tert-butyl, pentyl, cyclopropyl, cyclobutyl, cyclopentyl, and cyclohexyl.

"Lower alkyl" refers to an alkyl group having 1 to about 6 carbon atoms.

"Alkenyl" refers to a univalent aliphatic hydrocarbon group containing at least one carbon-carbon double bond and having from 2 to about 10 carbon atoms in the chain, and all combinations and subcombinations of chains therein. Exemplary alkenyl groups include, but are not limited to, vinyl, propenyl, butynyl, pentenyl, hexenyl, and heptnyl.

"Alkynyl" refers to a univalent aliphatic hydrocarbon group containing at least one carbon-carbon triple bond and having from 2 to about 10 carbon atoms in the chain, and combinations and subcombinations of chains therein. Exemplary alkynyl groups include, but are not limited to, ethynyl, propynyl, butynyl, pentynyl, hexynyl, and heptynyl.

"Alkylene" refers to a divalent aliphatic hydrocarbon group having from 1 to about 6 carbon atoms, and all combinations and subcombinations of chains therein. The alkylene group may be straight, branched, or cyclic. There may be optionally inserted along the alkylene group one or more oxygen, sulfur, or optionally substituted nitrogen atoms, wherein the nitrogen substituent is an alkyl group as described previously.

"Alkenylene" refers to a divalent alkylene group containing at least one carbon-carbon double bond, which may be straight, branched, or cyclic. Exemplary alkenylene groups include, but are not limited to, ethenylene (—CH═CH—) and propenylene (—CH═CHCH$_2$—).

"Cycloalkyl" refers to a saturated monocyclic or bicyclic hydrocarbon ring having from about 3 to about 10 carbons, and all combinations and subcombinations of rings therein. The cycloalkyl group may be optionally substituted with one or more cycloalkyl-group substituents. Exemplary cycloalkyl groups include, but are not limited to, cyclopropyl, cyclobutyl, cyclopentyl, cyclohexyl, and cycloheptyl.

"Acyl" means an alkyl-CO group wherein alkyl is as previously described. Exemplary acyl groups include, but are not limited to, acetyl, propanoyl, 2-methylpropanoyl, butanoyl, and palmitoyl.

"Aryl" refers to an aromatic carbocyclic radical containing from about 6 to about 10 carbons, and all combinations and subcombinations of rings therein. The aryl group may be optionally substituted with one or two or more aryl group substituents. Exemplary aryl groups include, but are not limited to, phenyl and naphthyl.

"Aryl-substituted alkyl" refers to a linear alkyl group, preferably a lower alkyl group, substituted at a terminal carbon with an optionally substituted aryl group, preferably an optionally substituted phenyl ring. Exemplary aryl-substituted alkyl groups include, for example, phenylmethyl, phenylethyl, and 3(4-methylphenyl)propyl.

"Heterocyclic" refers to a monocyclic or multicyclic ring system carbocyclic radical containing from about 4 to about 10 members, and all combinations and subcombinations of rings therein, wherein one or more of the members of the ring is an element other than carbon, for example, nitrogen, oxygen, or sulfur. The heterocyclic group may be aromatic or nonaromatic. Exemplary heterocyclic groups include, for example, pyrrole and piperidine groups.

"Halo" refers to fluoro, chloro, bromo, or iodo.

Compounds employed in methods of the invention (e.g., opioid receptor antagonists) may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S- or the R-configuration, as defined by the IUPAC 1974 Recommendations. Compounds may be of the D- or L-form, for example. It is well known in the art how to prepare and isolate such optically active forms. For example, mixtures of stereoisomers may be separated by standard techniques including, but not limited to, resolution of racemic form, normal, reverse-phase, and chiral chromatography, preferential salt formation, recrystallization, and the like, or by chiral synthesis either from chiral starting materials or by deliberate synthesis of target chiral centers.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

Compounds of the invention also encompass their salts. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts, such as alkylammonium salts. Some embodiments contemplate non-toxic, pharmaceutically acceptable salts as described herein, although other salts may be useful, as, for example, in isolation or purification steps. Salts include, but are not limited to, sodium, lithium, potassium, amines, tartrates, citrates, hydrohalides, phosphates and the like.

The compounds employed in methods of the invention may exist in prodrug form. As used herein, "prodrug" is intended to include any covalently bonded carriers which release the active parent drug or compounds that are metabolized in vivo to an active drug or other compounds employed in the methods of the invention in vivo when such prodrug is administered to a subject. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a subject, cleaves to form a free hydroxyl, free amino, or carboxylic acid, respectively. Other examples include, but are not limited to, acetate, formate, and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

IV. Methods of Administration and Other Formulation Considerations

Pharmaceutical compositions of the present invention comprise an effective amount of one or more candidate substances (e.g., a particle of the present invention) or additional agents dissolved or dispersed in a pharmaceutically acceptable carrier. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it needs to be sterile for such routes of administration. Particles of the present invention may be administered alone or as comprised in a composition (e.g., a pharmaceutical composition) orally, intraadiposally, intraarterially, intraarticularly, intracranially, intradermally, intralesionally, intramuscularly, intranasally, intraocularally, intrapericardially, intraperitoneally, intrapleurally, intraprostaticay, intrarectally, intrathecally, intratracheally, intraumbilically, intravaginally, intravenously, intravesicularly, intravitreally, liposomally, locally, mucosally, orally, parenterally, rectally, subconjunctival, subcutaneously, sublingually, topically, transbuccally, transdermally, vaginally, in creams, in lipid compositions, via a catheter, via a lavage, via continuous infusion, via infusion, via inhalation, via injection, via local delivery, via localized perfusion, bathing target cells directly, or by other method or any combination of the foregoing as would be known to one of ordinary skill in the art (see, for example, Remington's Pharmaceutical Sciences, 1990). In particular embodiments, a particle of the present invention may be formulated for oral delivery. In certain embodiments, intramuscular, intravenous, topical administration, or inhalation administration is contemplated. In certain embodiments, oral administration is contemplated. As noted, pharmaceutical compositions comprising a particle of the present invention are also contemplated, and such compositions may be adapted for administration via any method known to those of skill in the art, such as the methods described above.

In particular embodiments, a particle of the present invention or composition comprising such a particle is administered to a subject using a drug delivery device. Any drug delivery device is contemplated in this regard.

The actual dosage amount of an opioid receptor antagonist comprised in a particle of the present invention that is administered to a subject can be determined by physical and physiological factors such as body weight, severity of condition, the type of disease being treated, previous or concurrent therapeutic interventions, idiopathy of the patient and on the route of administration. The practitioner responsible for administration will typically determine the concentration of active ingredient(s) in a composition and appropriate dose(s) for the individual subject.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent, for example. The administration could be intraoperative or post-operative.

In certain embodiments, pharmaceutical compositions may comprise, for example, at least about 0.1% of an opioid receptor antagonist. In other embodiments, the opioid receptor antagonist may comprise between about 2% to about 75% of the weight of the unit, or between about 25% to about 60%, for example, and any range derivable therein. In other non-limiting examples, a dose may also comprise from about 10 µg/kg/body weight, 100 µg/kg/body weight, 200 µg/kg/body weight, 350 µg/kg/body weight, 500 µg/kg/body weight, 1 mg/kg/body weight, 5 mg/kg/body weight, 10 mg/kg/body weight, 50 mg/kg/body weight, to about 100 mg/kg/body weight or more of the opioid receptor antagonist per administration, or any range derivable therein. In a non-limiting example of a derivable range from the numbers listed herein, a range of about 0.1 mg/kg/body weight to about 10 mg/kg/body weight may be administered.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The opioid receptor antagonist comprised in a particle may be formulated into a composition, such as a pharmaceutical composition, in a free base, neutral, or salt form. Pharmaceutically acceptable salts are described herein.

In embodiments wherein a carrier is employed, such a carrier may be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. In particular embodiments, suspensions and capsules are contemplated. Oral compositions may be incorporated directly with the food of the diet. In certain embodiments, carriers for oral administration comprise inert diluents (e.g., glucose, lactose, or mannitol), assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Sterile injectable solutions may be prepared by incorporating a particle of the present invention in the required amount in the appropriate solvent with various of the other ingredients enumerated above, as required, followed by sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterilized liquid medium thereof. The liquid medium should be suitably buffered if necessary and the liquid diluent (e.g., water) first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

Certain embodiments of the present invention refer to aqueous formulations or solutions of methylnaltrexone, specifically. Such aqueous formulations may include a chelating agent, a buffering agent, an anti-oxidant and, optionally, an isotonicity agent, and may be pH adjusted to between about 3.0-3.5.

V. Combination Therapy

In order to enhance or increase the effectiveness of an opioid receptor antagonist comprised in a particle of the present invention, the particle may be combined with another therapy, such as another agent that combats and/or prevents a disorder mediated by opioid receptor activity. For example, a particle of the present invention may be provided in a combined amount with an effective amount of a second opioid receptor antagonist. Additionally, a particle of the present invention may be provided in a combined amount with an effective amount of an anti-cancer agent, as described in U.S. Patent Application No. 2006/0258696, PCT Publication No. WO 06/096626, or PCT Publication No. WO 07/053194, all hereby incorporated by reference. The second agent may be comprised in a second particle.

It is contemplated that combination therapy of the present invention may be used in vitro or in vivo. These processes may involve administering the agents at the same time or within a period of time wherein separate administration of the substances produces a desired therapeutic benefit. This may be achieved by contacting the cell, tissue, or organism with a composition, such as a pharmaceutically acceptable composition, that includes two or more agents, or by contacting the cell with two or more distinct compositions, wherein one composition includes one agent and the other includes another.

The particles of the present invention may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered about 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1, 2, 3, 4, 5, 6, 7 or 8 weeks or more, or any range derivable therein, prior to and/or after administering the candidate substance.

Various combination regimens of the agents may be employed. Non-limiting examples of such combinations are shown below, wherein a particle of the present invention is "A" and a second agent, such as a second opioid receptor antagonist, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Reagents used in each of these examples are commercially available.

Example 1

Preparation of Particles Comprising Methylnaltrexone

A procedure developed by the Alonso lab from the School of Pharmacy, University of Santiago de Compostela, Spain was employed (Calvo et al., 1997; Fernandez-Urrusuno et al., 1999).

Methylnaltrexone (MNTX) (Mallinckrodt Chemicals, St. Louis, Mo.) was dissolved in water and then incorporated in an aqueous pentasodium tripolyphosphate (TPP) solution. Under high-speed magnetic stirring of an aqueous chitosan solution, the MNTX-containing TPP solution was slowly added into the chitosan solution. Nanoparticles containing MNTX were then formed. The final ratio of chitosan:TPP:MNTX was approximately 5/1.8/3.2 (w/w/w). MNTX nanoparticles were collected by centrifugation, supernatants were discarded and the remaining nanoparticles were lyophilized.

Example 2

Preparation of Enterically Coated Particles Comprising Methylnaltrexone

Enterically coated MNTX nanoparticles were prepared by encapsulating the nanoparticles of Example 1 with a Eudagrit® L100 and Myvacet® 9-45 mixture. See, e.g., U.S. Pat. No. 6,608,075 and Yuan et al., 2000, each of which is incorporated herein by reference in its entirety. The final substance was the 30-80 mesh fraction which was 60% MNTX nanoparticles by weight. It was shown to decrease release of the drug at gastric pH by 90% based on the methods of the United States Pharmacopoeia/National Formulary (The United States Pharmacopeia, 1995). See also U.S. Pat. No. 6,608,075 and Yuan et al., 2000.

Example 3

Preparation of A Heteroparticulate Particle Comprising Methylnaltrexone

Methodology as described by Beck et al., 2004 was followed. To prepare the outer particles, a lipophilic solution consisting of Epikuron 170® (0.1532 g), a polymer (poly (caprolactone) (PCL) (MW=60,000 g/mol) or Eudragit® S100) (1.0 g) and acetone (267.0 ml) was used. This organic phase was added to an aqueous solution (533.0 ml) containing Tween 80® (0.1532 g) under moderate magnetic stirring. The solution was concentrated by evaporation under reduced pressure, and then the final volume was adjusted to 100 ml using acetone, corresponding to a polymer concentration of 10 mg/ml.

To prepare the inner particle, an MNTX solution (17 mM, 50 mL) was added to Aerosil® 200 (1.50 g). The mixture was fed into a mini-spray-dryer to produce particles having an MNTX core (feed rate: 3.0 ml/min; air flow rate: 500 NL/hr; atomizing air pressure: 200 kPa; inlet temperature: 170±4° C.; outlet temperature: 110±4° C.; nozzle diameter 0.7 mm).

The coating step was performed as follows: the MNTX particles (1.5 g) were rapidly dispersed into the outer particle suspension (50 mL) under magnetic stirring. This mixture was spray-dried to obtain heteroparticulate particles, wherein the inner particle comprised MNTX and the outer particles that surrounded the inner particle comprised a polymer suitable as an enteric coating (spray dryer conditions: feed rate: 3.0 ml/min; air flow rate: 500 NL/hr; atomizing air pressure: 200 kPa; inlet temperature: 170±4° C.; outlet temperature: 110±4° C.; nozzle diameter 0.7 mm).

This nanoparticles is pH-responsive. At pH 2.0 (in the gastric environment), the drug release was very low. At pH 7.4, the drug release was almost 100% in 15 min (The United States Pharmacopeia, 1995).

Example 4

In Vivo Study of Plasma Levels Upon Particle Administration

Abbreviations: N1-MNTX=particles of Example 2; N2-MNTX=particles of Example 3 using PCL.

Male Wistar strain rats, weighing between 200-300 g were used. Rats in group 1 (n=6) received 10 mg/kg regular MNTX (in distilled water); rats in group 2 (n=7) received 10 mg/kg N1-MNTX (in distilled water); rats in group 3 (n=5) received 10 mg/kg N2-MNTX (in solution with pH 2). Drugs were administered orally via a gavage tube in the morning at time 0. There were 6-8 rats per group.

Blood samples were collected from the tail vein for the measurement of plasma MNTX levels. The samples were typically collected every 30 min. from time 0 to time 360 min. Plasma MNTX levels were determined by high performance liquid chromatography (HPLC) adapted from a previously reported method (Osinski et al., 2002). The practical limit of detection for plasma samples was approximately 2 ng/mL (100 pg/injection).

MNTX plasma levels after oral administration of MNTX, N1-MNTX and N2-MNTX to rats are shown in Figure. Absorption of MNTX in both of the MNTX particle formulations (N1-MNTX and N2-MNTX) into the blood stream of rats was much more efficient than the absorption of aqueous MNTX. The chitosan/TPP/MNTX formulation (N1-MNTX) proved to be more efficient than the Epikuron 170® formulation (N2-MNTX), however both performed much better than non-particulate MNTX. These results demonstrate that particle formulations of methylnaltrexone and other opioid antagonists can greatly increase the absorption of these compounds into the central nervous system of mammals, thus decreasing the dose required to reach therapeutic plasma levels.

REFERENCES

The following references, to the extent that they provide exemplary procedural or other details supplementary to those set forth herein, are specifically incorporated herein by reference.

U.S. Pat. No. 3,723,440
U.S. Pat. No. 4,176,186
U.S. Pat. No. 4,311,833
U.S. Pat. No. 4,377,568
U.S. Pat. No. 4,457,907
U.S. Pat. No. 4,462,839
U.S. Pat. No. 4,518,433
U.S. Pat. No. 4,556,552
U.S. Pat. No. 4,606,909
U.S. Pat. No. 4,615,885
U.S. Pat. No. 4,670,287
U.S. Pat. No. 4,719,215
U.S. Pat. No. 4,861,781
U.S. Pat. No. 5,102,887
U.S. Pat. No. 5,270,328
U.S. Pat. No. 5,536,507
U.S. Pat. No. 5,567,423
U.S. Pat. No. 5,591,433
U.S. Pat. No. 5,597,564
U.S. Pat. No. 5,609,871
U.S. Pat. No. 5,614,222
U.S. Pat. No. 5,626,875
U.S. Pat. No. 5,629,001
U.S. Pat. No. 5,972,954
U.S. Pat. No. 6,274,591
U.S. Pat. No. 6,451,806
U.S. Pat. No. 6,469,030
U.S. Pat. No. 6,608,075
U.S. Published Appl. 2002/0028825
U.S. Published Appl. 2003/0022909
U.S. Published Appl. 2006/0105046
U.S. Published Appl. 2006/0258696
U.S. Published Appl. 2008/0064744
U.S. Published Appl. 2008/0113030
Beck et al., *J Microencapsulation,* 21:499-512, 2004.
Calvo et al., *J Appl Pol Sci.,* 63:125-32, 1997.
Fernandez-Urrusuno et al., *Pharm Res.,* 16:1576-81, 1999.
*Handbook of Pharmaceutical Salts: Properties, Selection and Use* (Stahl and Wermuth, Eds.), Verlag Helvetica Chimica Acta, 2002.
Osinski et al., *J Chromatogr B,* 780:251-9, 2002.
PCT Appln. WO 06/096626
PCT Appln. WO 07/053194
PCT Appln. WO 98/25613
PCT Appln. WO 99/22737
Remington's: *The Science and Practice of Pharmacy,* 19$^{th}$ Ed., Mac Publishing Co., Easton, Pa., 1676-1692, 1995.
Remington's Pharmaceutical Sciences, 18th Ed. Mack Printing Company, 1289-1329, 1990.
Sarmento et al., *Biomacromolecules,* 8:3054-60, 2007.
The United States Pharmacopeia: The National Formulary. Rockville: United States Pharmacopeial Convention, Inc, 1793-1799, 1995.
Yuan et al., *Clin. Pharmacol. Ther.,* 61:467-475, 1997
Yuan et al., *Clin. Pharmacol. Ther.,* 67:398-404, 2000.

The invention claimed is:

1. An enterically-coated particle comprising at least one opioid receptor antagonist, at least one hydrophilic additive that is negatively charged at acidic and neutral pH that is pentasodium tripolyphosphate (TPP), and at least one hydrophilic additive that is positively charged at acidic and neutral pH that is chitosan;
wherein the enteric coating comprises a methacrylic acid-methyl methacrylate copolymer.

2. The enterically-coated particle of claim 1, wherein the opioid receptor antagonist is a positively-charged peripheral opioid receptor antagonist.

3. The enterically-coated particle of claim 2, wherein the peripheral opioid receptor antagonist is a quaternary morphinan derivative, a N-methyl-6-carboxy-normorphinan derivative, or a quaternary benzomorphan derivative.

4. The enterically-coated particle of claim 3, wherein the quaternary morphinan derivative is a quaternary salt of N-methylnaltrexone, N-methylnaloxone, N-methylnalorphine, N-diallylnormorphine, N-allyllevellorphan, or N-methylnalmefene.

5. The enterically-coated particle of claim 3, wherein the quaternary benzomorphan derivative is selected from the group consisting of 2'-hydroxy-5,9-dimethyl-2,2-diallyl-6,7-benzomorphanium bromide; 2'-hydroxy-5,9-dimethyl-2-n-propyl-2-allyl-6,7-benzomorphanium bromide; 2'-hydroxy-5,9-dimethyl-2-n-propyl-2-propargyl-6,7-benzomorphanium bromide; and 2'-acetoxy-5,9-dimethyl-2-n-propyl-2-allyl-6,7-benzomorphanium bromide.

6. The enterically-coated particle of claim 1, wherein the particle comprises two or more opioid receptor antagonists.

7. The enterically-coated particle of claim 1, wherein a diameter of the enterically-coated particle is between about 30-1000 nm.

8. The enterically-coated particle of claim 1, wherein a weight percentage of total opioid receptor antagonist in the enterically-coated particle ranges from about 8-35.

9. The enterically-coated particle of claim 1, further defined as a time release composition, wherein the time release composition is formulated to release the opioid receptor antagonist over time.

* * * * *